United States Patent [19]

Deal et al.

[11] Patent Number: 4,786,592
[45] Date of Patent: Nov. 22, 1988

[54] *NEISSERIA GONORRHOEAE* LECTIN USEFUL AS A VACCINE AND DIAGNOSTIC MARKER AND MEANS FOR PRODUCING THIS LECTIN

[75] Inventors: Carolyn D. Deal, San Diego; Magdalene Y. H. So, Cardiff; H. Steven Seifert, Del Mar, all of Calif.

[73] Assignee: Scripps Clinic and Research Foundation, La Jolla, Calif.

[21] Appl. No.: 907,115

[22] Filed: Sep. 12, 1986

Related U.S. Application Data

[63] Continuation-in-part of Ser. No. 875,477, Jun. 18, 1986, abandoned.

[51] Int. Cl.$^4$ .................. A61K 39/095; C07H 21/00; C12N 15/00; G01N 33/571
[52] U.S. Cl. .......................................... 435/7; 424/92; 435/68; 435/172.1; 435/172.3; 435/253; 435/317.1; 435/871; 436/511; 436/827; 530/396; 536/27; 935/11; 935/12; 935/29; 935/72
[58] Field of Search ............... 424/92; 435/68, 172.1, 435/172.3, 253, 317.1, 7, 871; 530/396; 536/27; 935/11, 12, 29, 72; 436/827, 511

[56] References Cited

U.S. PATENT DOCUMENTS

| 4,066,744 | 1/1978 | Price | 424/92 X |
| 4,115,543 | 9/1978 | Wallace | 424/92 X |
| 4,203,971 | 5/1980 | Buchanan | 424/92 |
| 4,237,224 | 12/1980 | Cohen | 435/68 |
| 4,239,749 | 12/1980 | Buchanan | 424/92 |
| 4,443,431 | 4/1984 | Buchanan | 424/92 |

OTHER PUBLICATIONS

Perrollet, H. et al., The Lancet, vol. 1, No. 8492, 1269–1270 (May 31, 1986).
Heckels, J. E., J. Gen. Microbiol., vol. 99, Part 2, 333–341, (1977).
Buchanan, T. M. et al., Infection and Immunity, 32(3), 985–994 (Jun. 1981).

*Primary Examiner*—Sidney Marantz
*Attorney, Agent, or Firm*—Dressler, Goldsmith, Shore, Sutker & Milnamow

[57] ABSTRACT

A bacterial lectin isolatable from *Neisseria gonorrhoeae* is disclosed. This lectin binds to gonococcal carbohydrates such as gangliotetraosylceramide, has a relative molecular weight of about 22,400 daltons, and an isoelectric pH value in the range of about 6.1 to about 6.4. The disclosed lectin is useful as a constituent of a vaccine against gonorrhea and as a diagnostic means for gonorrhea. A method for isolating this lectin is also disclosed, as well as means for producing it.

23 Claims, 5 Drawing Sheets

NEISSERIA GONORRHOEAE LECTIN USEFUL AS A VACCINE AND DIAGNOSTIC MARKER AND MEANS FOR PRODUCING THIS LECTIN

CROSS-REFERENCE TO RELATED APPLICATION

This application is a continuation-in-part of copending application U.S. Ser. No. 875,477, filed on 18 June 1986 now abandoned.

TECHNICAL FIELD

This invention relates to a lectin suitable for use in an inoculum or a vaccine against *Neisseria gonorrhoeae*, to a vaccine containing the lectin and to a method of diagnosing gonorrhea. More specifically, this invention relates to a *Neisseria gonorrhoeae* lectin obtainable from gonococci, a method of isolating the lectin, to an inoculum and/or a vaccine prepared therefrom, and to means for producing such lectin.

BACKGROUND ART

The annual incidence of reported infections by *Neisseria gonorrhoeae* (N.g.) is estimated to be about two million cases. A gonococcal infection in men usually results in a relatively uncomplicated urogenital infection. Disseminated gonococcal infection is reported to occur in 1 to 3% of those with gonorrhea, but the morbidity of this disease with current therapy is slight.

On the other hand, in women infected with gonorrhea, salpingitis occurs in 10 to 20%, and even when adequately treated, may result in recurrent salpingitis, ectopic pregnancy, and infertility. It is estimated that salpingitis leads to 1.8 million office visits to private physicians and 220,000 hospitalizations each year in the United States.

The control of gonorrhea by public health measures to date has been difficult. A vaccine composed of whole, killed gonococci has not been efficacious, Greenburg et al. "Preliminary Studies on the Development of a Gonococcal Vaccine," Bull. Wld. Hlth. Org. 45:531 (1971).

Penicillin and tetracycline resistant strains of gonococci have also emerged.

Gonococcal infection involves colonization of the mucous membranes by the bacterium, a process mediated by the adhesion of the colonizing cell to the surface membrane. The term "adhesion" describes the relatively stable attachment of bacteria to surfaces. Any structures responsible for such adhesive activities are termed adhesins.

The gonococcal pilus is an adhesin having a filamentous structure composed of repeating identical subunits (pilin). In the MS11 strain of N.g., each pilin has a molecular weight of approximately 18,000 daltons. The attachment of the gonococci to the epithelial surface can be blocked by an anti-pilus antibody. In addition to blocking cell attachment, antibodies raised against pilus protein are also opsonic, i.e., they mediate the killing of the invading bacteria by the phagocytes in the blood. However, the use of pilus immunogens as vaccines has been rendered impractical by the lack of serological cross-reactivity of pili made by different strains of N.g.

We have found that eukaryotic cell surface glycosphingolipids, e.g., lactosylceramide, isoglobotriosylceramide, gangliotriosylceramide, and gangliotetraosylceramide, are involved in recognition and adhesion of N.g., and further that the glycolipid-directed recognition is mediated by a heretofore unreported bacterial lectin, a bacterial protein having the ability to recognize and bind to specific saccharide sequences (carbohydrate structures). This bacterial lectin, when used as a constituent of an inoculum, a vaccine, or in a diagnostic assay, does not suffer from the aforementioned shortcomings of a pilus immunogen.

SUMMARY OF THE INVENTION

The present invention contemplates an isolated bacterial lectin, designated GCL-1. This lectin is obtainable from gonococci, binds to eukaryotic carbohydrates, and has a relative molecular weight of about 22,400 daltons. The isoelectric pH value for this lectin is in the range of about 6.1 to about 6.4. The lectin has the ability to specifically bind to gangliotetraosylceramide, and is useful as a constituent of an inoculum or a vaccine against gonorrhea. This lectin is also useful as a diagnostic means for gonorrhea. This lectin can be used in its isolated form or as a pharmaceutically acceptable salt thereof.

Additionally, the present invention contemplates an inoculum and a vaccine constituted by the aforementioned isolated lectin or a pharmaceutically acceptable salt thereof and a pharmaceutically acceptable carrier therefor. Also contemplated is a method of immunizing against gonococcal infections by administering to a patient an effective amount of the isolated lectin or its aforementioned salt in a pharmaceutically acceptable carrier or diluent.

The present invention further contemplates an isolated DNA fragment coding the GCL-1 lectin, the same DNA fragment present within a biological host and a culture wherein the aforementioned biological host is present together with a growth medium suitable for expression of GCL-1-coding gene present in an expression vector and while contained within a suitable expression medium.

BRIEF DESCRIPTION OF THE DRAWINGS

In the drawings forming a portion of the disclosure of this invention.

Lane A contains purified pilin protein having a relative molecular weight of about 18,000 daltons.

Lane B contains a sample of the proteins remaining after the lectin of this invention (GCL-1) was affinity absorbed from the crude GCL-1 extract produced in Example 1. GCL-1 is not shown to be present at a level within the method's limit of detection. However, pilin protein can be seen at the 18,000 molecular weight position.

Lane C contains affinity isolated GCL-1 present at the 22,400 dalton position. No ubstantial amount of pilin or pilin associated protein is present.

Lane D contains the eluate of a crude GCL-1 extract solution subjected to globoside affinity isolation as described in Example 1. This solution was used as a control to detect non-specific binding to the glycolipid affinity matrix. The absence of a significant amount of GCL-1 in this lane indicates that the binding of GCL-1 to the gangliotetrasylceramide affinity matrix was a specific lectin-ligand interaction.

Lane E contains the following molecular weight marker proteins: α-lactalbumin, 14; soybean trypsin inhibitor, 20; trypsinogen, 24; carbonic anhydrase, 29; glyceraldehyde-3-phosphate dehydrogenase, 36; egg albumin, 45; and bovine albumin, 66, all in units of one thousand daltons.

Figure 2:
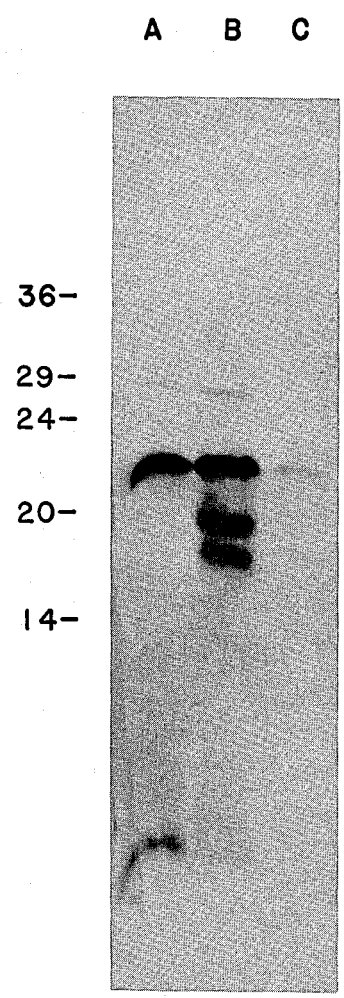

FIG. 2 is a photograph of a Western blot analysis of GCL-1 containing solutions using rabbit anti-GCL-1 antibodies raised to affinity isolated GCL-1. Indicated to the left of the blots are the expected positions, in thousands of daltons, of proteins having the indicated relative molecular weights.

Lane A contains a sample of the crude GCL-1 extract produced in Example 1. GCL-1 is the major protein band having a relative molecular weight of about 22,400 daltons. Two minor protein bands believed to be pilin associated lectins appear at about the 29,000 dalton position and above the 36,000 dalton position.

Lane B contains a sample of the pilin protein containing pellet formed in Example 1. While GCL-1 is present in a substantial amount, other pilin and pilin associated proteins are also present in substantial amounts.

Lane C contains affinity isolated GCL-1 substantially free of other pilin associated proteins.

Figure 3:

FIG. 3 is a photograph of a Western blot showing that rabbit anti-GCL-1 antibodies crossreact with a protein produced by *Morexella bovis* that has the same relative molecular weight as GCL-1 produced by N.g. (arrow). Lane A contains a crude GCL-1 extract prepared according to Example 1 of N.g. strain MS11 non-piliated variant B2. Lane B contains an extract prepared in a similar manner from *Morexella bovis*.

Figure 4:
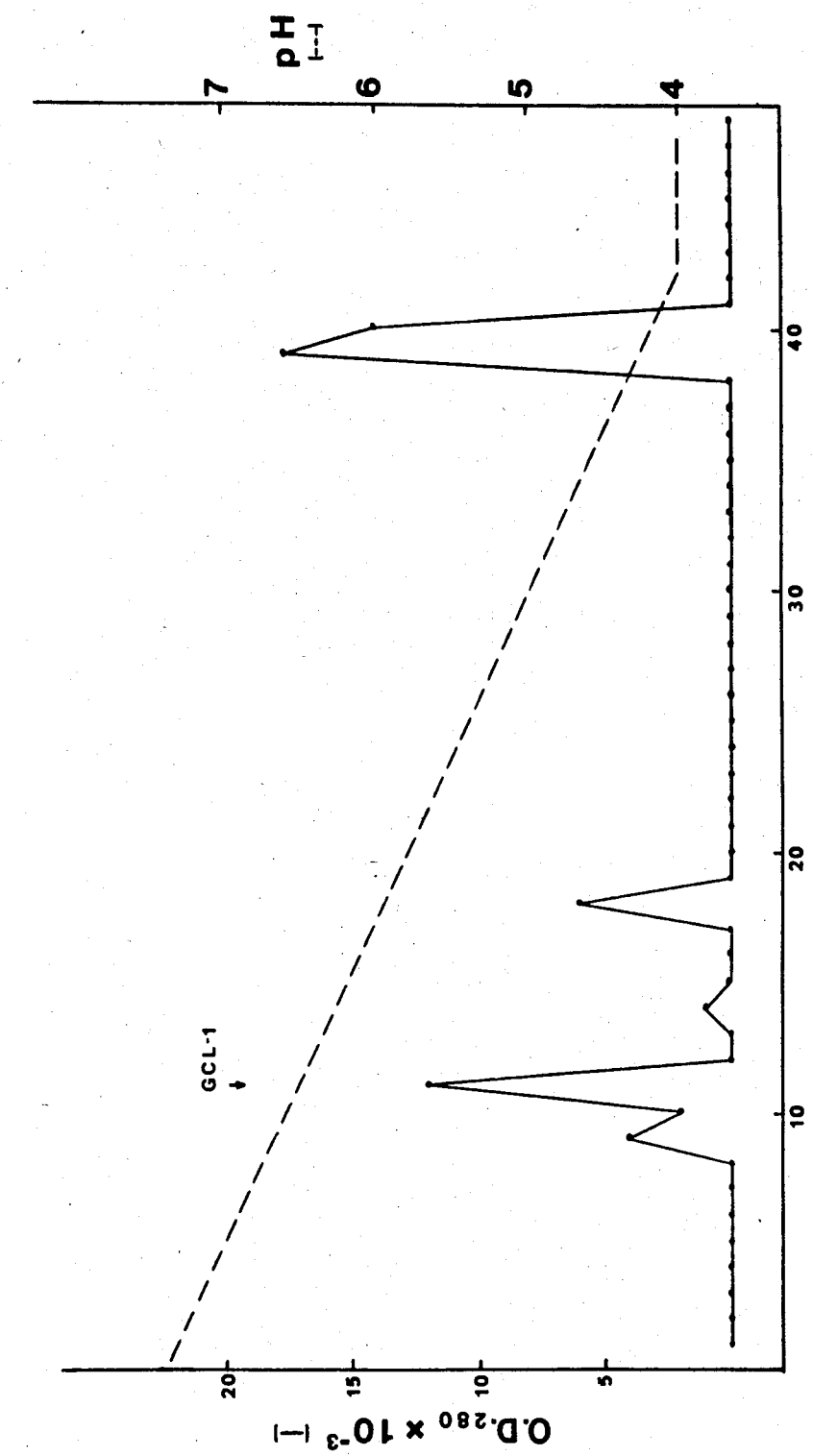

FIG. 4 is a graph illustrating the purification of the crude GCL-1 extract of EXAMPLE 1 by elution from a Mono P chromatofocusing column with the application of a pH gradient. The eluant was monitored for protein by measuring the optical density at an adsorbance of 280 nanometers (O.D. 280) as fractions eluted over a linearly decreasing pH gradient. Peak fractions containing the GCL-1 elute off the chromatofocusing column at a pH range which trails slightly higher than about 6.1 to 6.4 and is indicated by the arrow.

Figure 5:
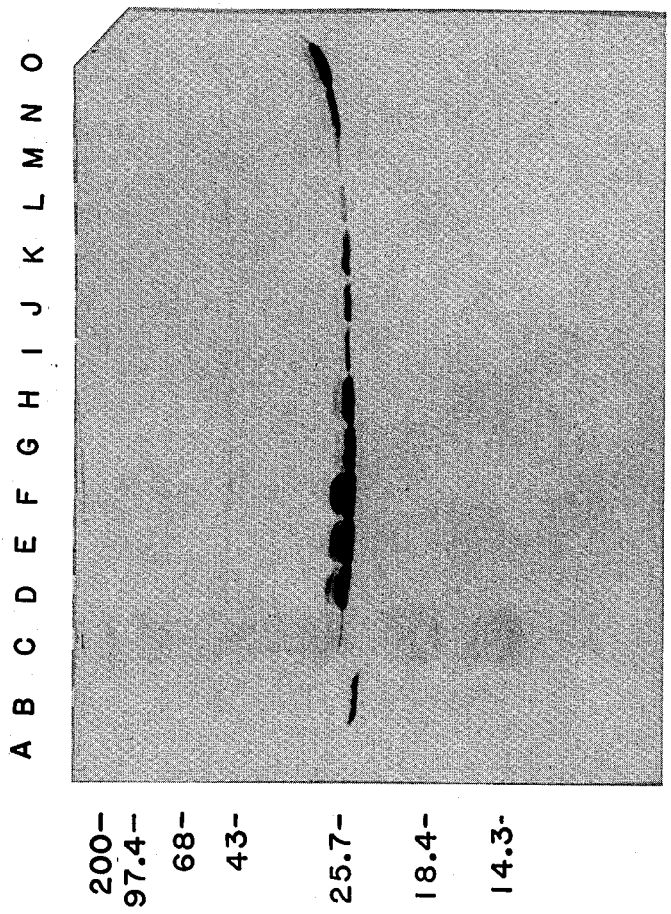

FIG. 5 is a photograph of a Western blot analysis of GCL-1 containing solutions using rabbit anti-GCL antibodies raised to the GCL-1 isolated by chromatofocusing. Indicated to the left of the blots are the expected positions, in thousands of daltons, of proteins having the indicated relative molecular weights.

Lane A contains a sample of a culture of *Escherichia coli* containing the plasmid pHSS6 described in EXAMPLE 5 but lacking any gonococcal DNA inserts. The sample was lysed in SDS-PAGE sample buffer, resolved by electrophoresis and Western blotted as described in EXAMPLE 5.

Lane B contains a sample of the crude GCL-1 extract produced in EXAMPLE 1 and analyzed as described for Lane A. GCL-1 is the major protein band having a relative molecular weight of about 22,400 daltons.

Lane C contains the following prestained molecular weight marker proteins (Bethesda Research Laboratories, Gaithersburg, MD); myosin, 200; phosphorylase b, 97.4; bovine serum albumin, 68; ovalbumin, 43; chymotrypsinogen, 25.7; β-lactoglobulin, 18.4; and lysozyme, 14.3, all in units of one thousand daltons.

Lanes D through O contain samples from individual cultures of *E. coli* containing the plasmid pHSS6 with gonococcal DNA inserted therein as described in EXAMPLE 5 and which have been analyzed as described for Lane A.

DETAILED DESCRIPTION OF THE INVENTION

DEFINITIONS

The term "antibody" in its various grammatical forms as used herein refers to an immunoglobulin or any fragment thereof containing a biologically active antibody combining site that specifically binds an antigen.

The term "complex" as used herein refers to the product formed when a lectin specifically binds to a ligand.

The term "immunoreactant" as used herein refers to the product of an immunological reaction, i.e., that entity produced when an antigen is immunologically bound by an antibody.

The term "isolated" as used herein with reference to a lectin refers to such a lectin that is substantially free from other gonococcal proteins. When this term is used with respect to the antibody preparations of this invention, this term refers to anti-GCL-1 antibodies that are substantially free from other anti-gonococcal protein antibodies.

The term "ligand" refers to a molecule having a carbohydrate structure that is specifically bound by lectin.

The term "pharmaceutically acceptable salt," as used herein, refers to a non-toxic alkali metal, alkaline earth metal or ammonium salt of the isolated lectin. Such salts are commonly used in the pharmaceutical industry and include the sodium, potassium, lithium, calcium, magnesium, and ammonium salts, and the like, which are prepared by methods well known in the art. The term also includes non-toxic acid addition salts which are generally prepared by reacting the lectin of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and the like.

The isolated gonococcal carbohydrate-binding protein, or lectin, contemplated by the present invention has a relative molecular weight of about 22,400 daltons as determined by sodium dodecylsulfate-polyacrylamide gel electrophoresis (SDS-PAGE) using α-lactalbumin, soybean trypsin inhibitor, trypsinogen, carbonic anhydrase, glyceraldehyde-3-phosphate dehydrogenase, egg albumin, and bovine albumin as comparative molecular weight standards. That is, the electrophoretic mobility of the present lectin (GCL-1) is between that of soybean trypsin inhibitor and trypsinogen. The technique and reliability of molecular weight determination by SDS-PAGE are well known in the art. Weber et al., J. Biol. Chem. 244:4406–4412 (1969), Zwaan, J., Anal. Biochem. 21:155–168 (1967).

GCL-1 can also be characterized further as having an isoelectric pH value of about 6.1 to about 6.4. The isoelectric pH or isoelectric point (pI) of a protein is that pH value at which the protein has no net electrical charge. Thus, at the isoelectric point, the protein does not move in an electric field. Methods for determining a protein's isoelectric pH value using polyacrylamide gels are well known in the art. Allen, R. C. and Maurer, H. R., *Electrophoresis and Isoelectric Focusing in Polyacrylamide Gel*, Walter de Gruyter, New York (1984); Arbuthnot, J. P. and Beeley, J. A., *Isoelectric Focusing*, Butterworths, London (1975).

GCL-1 also specifically binds to the glycosphingolipids lactosylceramide, isoglobotriosylceramide, gangliotriosylceramide and gangliotetraosylceramide.

Methods for determining the ability of a lectin to specifically bind a carbohydrate ligand are well known in the art. Those methods include binding inhibition studies of red blood cell agglutination or polysaccharide precipitation by the involved lectin. Affinity chromatography using either lectin or carbohydrate ligand as affinity absorbent can also be used for this purpose.

Typically, a known amount of GCL-1 is admixed with a predetermined amount of the glycosphingolipid. The admixture is maintained under biological assay conditions for a predetermined time period from minutes to hours, such as about 10 minutes to about 16–20 hours, that is, for a time period sufficient for GCL-1 to form a complex with the glycosphingolipid ligand.

Biological assay conditions are those that maintain the biological activity of the isolated lectin of this invention and its target ligands. Such assay conditions include a temperature range of about 4° C. to about 45° C., a pH value range of about 5 to about 9, and an ionic strength varying from that of distilled water to that of about one molar sodium chloride. Methods for optimizing such conditions are well known in the art.

The presence of GCL-1 containing complex that is formed is then assayed, either directly or indirectly, by assay techniques well known in the art.

Methods for providing the glycosphingolipids to which GCL-1 specifically binds are well known in the art. See, for example, Hansson et al., FEBS 170:15–18 (1984); Breimer et al., J. Biochem. 90:589–609 (1981); Karlsson and Larson, J. Biol. Chem. 257:557–568 (1982); Breimer et al., Biomed. Mass. Spectrom. 6:231–241 (1979); Hanson et al., Biochem. Biophys. Acta 750:214–216 (1983).

Another aspect of the invention pertains to a process for isolating GCL-1. This process entails fractionation of a solution containing this lectin while utilizing its above-described properties.

Specifically, solutions containing GCL-1 are first obtained by extraction of surface protein from N.g. To that end, the surface protein is sheared from N.g., typically by vortexing N.g. in an isotonic, non-denaturing buffer solution. Residual cells and debris are separated from the obtained solution by centrifugation. The produced supernatant liquor contains the GCL-1 protein, which is then recovered.

The various methods of gel filtration, gel chromatography, chromatofocusing, ultrafiltration, electrophoretic mobility, ion exchange, and the like, such as are known for protein fractionations, can then be used to separate a protein with the above described characteristics from other proteins present.

For instance, it is well known in the art that two dimensional polyacrylamide gel electrophoresis (2D-PAGE) methods involving two different electrophoretic separation techniques can be used to reproducibly isolate proteins from complex biological sources. Proteins in a solution are separated according to their respective isoelectric points by isoelectric focusing (IEF) in the first dimension, and then according to molecular weight by SDS-PAGE in the second dimension. Since the protein resolution is based on unrelated characteristics in each dimension, a substantially uniform distribution of discrete protein spots across a two dimensional gel is obtained. The discrete spot corresponding to a protein having the aforesaid isoelectric point and molecular weight is isolated as the lectin GCL-1 which, in turn, is then recovered from the gel by conventional techniques.

Alternatively GCL-1 may be separated from other proteins present in the aforementioned supernatant liquor by liquid chromatography chromatofocusing. This method separates proteins according to differences in their isoelectric points. By virtue of the pH gradient which flows through the column the proteins are focused and eluted in the order of their isoelectric points. Fractions corresponding to the aforesaid isoelectric point range are collected and the GCL-1 is recovered from the collected fractions by conventional techniques.

GCL-1 may also be isolated by subjecting a liquid containing this protein to one or more known methods for isolating a protein having the ability to specifically bind a ligand, such as affinity chromatography, affinity adsorption, and the like. When this alternative approach to isolation is used, typically a liquid containing GCL-1 is admixed with a solid-matrix-affixed ligand such as gangliotetraosylceramide. The obtained admixture is maintained under biological assay conditions for a time period sufficient for the GCL-1 to specifically bind to the solid-matrix-affixed ligand to form a solid phase complex. Non-specifically bound protein is then separated from the solid phase complex, usually by washing or rinsing with a buffer. Thereafter, GCL-1 is dissociated from the solid phase affixed ligand and eluted in isolated form.

In addition, immunochemical methods can be used to isolate GCL-1 from a liquid containing the lectin using the antibodies described hereinbelow. Such methods, e.g., immunoaffinity, immunoadsorption, and the like, are performed in a manner similar to that described above for glycolipid ligand-based affinity purification.

GCL-1 can also be produced in isolated form using well known recombinant DNA techniques. Briefly, DNA from N.g. is isolated and fragmented either by shearing or by restriction endonuclease digestion. The fragments are inserted into plasmid vectors such as pHSS6 or phage vector lambda. The insert containing vectors are introduced into a compatible host and propagated therein. The vector-containing hosts are subsequently cloned and the clones are assayed for the presence of plasmids containing the GCL-1 gene.

The cloned vector containing the GCL-1 gene may then be used as an expression vector to express the GCL-1 gene product directly. In some cases it is desirable to manipulate the GCL-1 gene further to accommodate expression in a different vector or in a different biological host.

The GCL-1 gene is then isolated from a plasmid containing the gene and recombined with appropriate nucleotide sequences to form a transcription-translation expression vector. The GCL-1 expression vector is then introduced into an appropriate transcription-translation prokaryotic expression medium such as a bacterium host, eukaryotic expression medium such as a yeast or mammalian host [e.g., Chinese hamster ovary (CHO) cells], or an in vitro medium such as that described by DeVries and Zubay, Proc. Natl. Acad. Sci. U.S.A. 57:267 (1967).

In a further aspect of this invention, the lectin of this invention or its salt is used in a pharmaceutically acceptable diluent or carrier to form an inoculum or a vaccine that, when administered to a patient in an effective amount, is capable of inducing antibodies that immunoreact with GCL-1 on the surface of N.g., thereby precluding adhesion to a surface membrane.

The term "inoculum" in its various grammatical forms is used herein to describe a composition containing a lectin of this invention as an active ingredient used for the induction of antibodies against GCL-1.

The inoculum can be used to produce antibodies in mammals such as mice, rabbits, goats, horses, and the like, for use in diagnostic assays that detect N.g. cells expressing GCL-1. Inocula can also be used as vaccines containing effective amounts of the lectin of this invention to protect the vaccinated individuals from infection with gonococcus and thus prevent a gonorrhea infection. Booster injection or injections can be given as well if needed.

The term "vaccine" in its various grammatical forms is used herein in relation to the protection of a human. The term "inoculum" in its various grammatical forms as used herein also describes a composition containing the protein of this invention as an active ingredient used for the generation of antibodies that immunologically bind to gonococcal GCL-1. A vaccine and an inoculum may thus contain the identical ingredients. The contemplated end uses are different, however.

The effective amount of isolated GCL-1 per unit dose depends, among other things, on the species of animal inoculated, the body weight of the animal, and the chosen inoculation regimen as is well known in the art. Inocula typically contain GCL-1 concentrations of about 10 micrograms to about 500 milligrams per inoculation (dose), preferably about 100 micrograms to about 100 milligrams per inoculation.

The term "unit dose" refers to physically discrete units suitable as unitary dosages for animals, each unit containing a predetermined quantity of active material calculated to produce the desired therapeutic effect in association with the required diluent, i.e., carrier or vehicle. The specifications for the novel unit dose of this invention are dictated by and are directly dependent on (a) the unique characteristics of the active material and the particular immunologic effect to be achieved, and (b) the limitations inherent in the art of compounding such active material for immunologic use in humans, as disclosed in detail in the specification, these being features of the present invention.

Inocula are typically prepared from the isolated bacterial lectin of this invention by suspending the lectin in a physiologically tolerable diluent such as water, saline or phosphate-buffered saline (PBS). Additives customarily used in vaccines or inocula may also be present, if desired. Illustrative of such additives are stabilizers such as lactose or sorbitol, and adjuvants such as aluminum hydroxide, sulfate or phosphate, an alum, or an alginate. Precipitated aluminum phosphate (AlPO$_4$) is a particularly suitable adjuvant for a vaccine, while complete Freund's adjuvant (CFA) and incomplete Freund's adjuvant (IFA) are preferred for use in inocula.

Vaccines and inocula of the present invention may be administered by injection, usually intramuscularly or subcutaneously, orally by means of an enteric capsule or tablet, as a suppository, as a nasal spray, and by other suitable routes of administration.

Antibodies induced by (raised to) the bacterial lectin of this invention in isolated form constitute still another embodiment of this invention. The isolated antibody preparations of this invention only exhibit substantially anti-gonococcus activity against GCL-1.

Antibodies against GCL-1 in isolated form are raised in mammals such as rabbits, goats, horses and the like by immunization, using the inocula described hereinbefore. Isolated antibody preparations can also be produced by immunoaffinity purification using the isolated bacterial lectin of this invention by methods well known in the art.

Isolated anti-GCL-1 antibody preparations can also be prepared using the hybridoma technology described by Niman et al., Proc. Natl. Acad. Sci. USA 82:7924–7928 (1985), incorporated herein by reference to the extent pertinent.

To form the hybridoma from which the monoclonal antibody is produced, a myeloma or other self-perpetuating cell line is fused with lymphocytes obtained from the spleen of a mammal hyperimmunized with GCL-1.

It is preferred that the myeloma cell line be from the same species as the lymphocytes. A mouse of the strain 129 GlX+ is the preferred mammal. Suitable mouse myelomas for use in the present invention include the hypoxanthine-aminopterin-thymidine-sensitive (HAT) cell lines P3X63-Ag8.653 (ATCC CRL 15080), and Sp2/0-Ag14 (ATCC CRL 1581).

Spleenocytes are typically fused with myeloma cells using polyethylene glycol (PEG) 1500. Fused hybrids are selected by their sensitivity to HAT. Hybridomas producing the antibodies of this invention are identified using the anti-GCL-1 enzyme linked immunosorbent assay (ELISA) described herein.

Monoclonal antibodies can be obtained not only from hybridoma culture supernatants, but may also be obtained in generally more concentrated form from ascites fluid of mammals into which the desired hybridoma has been introduced. Production of monoclonal antibodies using ascites fluid is well known in the art and need not be dealt with further herein.

The isolated bacterial lectin of the present invention is particularly useful for determining the presence and amount of anti-GCL-1 antibodies in a body sample such as blood, serum or plasma.

In one embodiment, the present invention contemplates a method of determining the presence of anti-GCL-1 antibodies in a body sample comprising the following steps:

(a) A body sample to be assayed is provided. Typically such sample is provided as a known amount of blood and more preferably as serum or plasma. Methods for providing samples of blood, serum and plasma are well known in the art.

(b) Next, a predetermined amount of the isolated bacterial lectin of this invention is provided.

(c) Thereafter the body sample is admixed with the isolated bacterial lectin to form an immunoreaction admixture.

(d) The obtained admixture is maintained under biological assay conditions for a predetermined period of time from minutes to hours. A time period of about 10 minutes to about 16–20 hours usually is sufficient for any anti-GCL-1 antibodies present in the sample to immunologically bind to the lectin to form immunoreactant.

The biological assay conditions for immunoreactions are similar to those described for lectin-ligand binding assays.

(e) The admixture maintained under the biological assay conditions is then assayed for the presence of any immunoreactant that has been formed during the aforementioned maintainance period. The presence of the immunoreactant is an indication that anti-GCL-1 antibodies are present in the sample.

Assaying for the presence of anti-GCL-1 antibody containing immunoreactant, either directly or indirectly, can be accomplished by assay techniques well known in the art. For example, a homogenous assay system such as those described in U.S. Pat. Nos. 4,536,479; 4,233,401; 4,233,402 and 3,996,345 may be used.

In preferred embodiments, the presence of anti-GCL-1 antibody bound to lectin is assayed by the following steps:

(i) A body sample is combined with biologically active labeled antibodies that bind to any human immunoglobulin that may be present in the body sample to form an immunoreactant. The labeled antibodies are capable of signaling the presence of the antibodies in an immunoreactant.

(ii) The labeled antibody/body fluid sample admixture so formed is maintained under biological assay conditions for a predetermined time period sufficient for the antibodies to form an immunoreactant with any anti-GCL-1 antibodies present as first immunoreactant. Immunoreaction can be accomplished in a manner similar to that described in step (d), above.

In the particularly preferred assays, the lectin of this invention and the labeled antibodies are thus immunologically bound to any anti-GCL-1 antibodies present in the body fluid sample thereby forming a sandwich immunoreactant that contains a label bound as part thereof. That is, a sandwich immunoreactant that contains a label is formed when one molecule of anti-GCL-1 antibody immunoreacts (1) as a antibody with the lectin of this invention and (2) as an antigen with a labeled antibody. In preferred embodiments, any labeled antibodies that do not form a part of the immunoreactant (i.e., those not immunologically bound to anti-GCL-1 antibodies) are separated from the immunoreactant, preferably by washing, prior to assaying for the presence of labeled antibody.

(iii) An assay is then made for the presence of the labeled antibody bound as part of the immunoreactant that contains anti-GCL-1 antibody. This provides an assay for the presence of anti-GCL-1 antibodies in the body sample. The amount of the labeled antibody bound as part of the immunoreactant is determined and this determination is used to quantify the amount of anti-GCL-1 antibodies in the sample. That amount can be zero, of course, thereby indicating no anti-GCL-1 antibodies are present in the sample, within the limits that can be detected. Methods for assaying for the presence and amount of a labeled second antibody depend on the label used, such labels and assay methods being well known in the art.

The labeling of proteinaceous antibodies also is a well known expedient. For instance, antibodies produced by hybridomas can be labeled by metabolic incorporation of isotope containing amino acids provided as a component in the tissue culture medium. See, for example, Galfre, G. and Milstein, C., Meth. Enzymol. 73:3–46 (1981). The techniques of protein conjugation or coupling through activated functional groups are particularly applicable. See, for example, Aurameas, et al., Scand. J. Immunol. 8, Suppl. 7: 7–23 (1978) and U.S. Pat. No. 4,493,795 both of which are incorporated herein by reference. In addition, site-directed coupling reaction can be carried out so that the label does not substantially interfere with the immunoreaction of the second antibody with its target antigen. See, for example, Rodwell et al., Biotech. 3:889–894 (1985).

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamin-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", *The Antibody as a Tool*, Marchalonis et al., Eds., Wiley & Sons Ltd., New York. N.Y. (1982), pp. 189–231, which is incorporated herein by reference.

In preferred embodiments the indicating group is an enzyme, such as horseradish peroxidase (HRP), glucose oxidase, or the like. Where the principal indicating group is an enzyme such as horseradish peroxidase (HRP) or glucose oxidase, additional reagents are required to visualize the fact that a antibody-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents.

An exemplary radiolabeling agent is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$ Another group of useful indicating groups are those elements such $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium.

The assay methods and systems of the present invention can utilize the lectin or anti-lectin antibodies of this invention affixed to solid matrix to form a solid support.

The lectin or anti-lectin antibodies are typically affixed to the solid matrix by adsorption from an aqueous medium although several modes of adsorption, as well as other modes of affixation, well known to those skilled in the art can be used. Exemplary of such modes are the reaction of the lectin or anti-lectin antibodies with the reactive carboxyl functionality produced by the reaction of cyanogen bromide with glucose-containing matrices such as cross-linked dextrose or cellulose. Gluteraldehyde as a linking is discussed hereinafter in conjunction with latex particles and the like.

Useful solid matrices are well known in the art. Such materials include the cross-linked dextran available under the trademark SEPHADEX from Pharmacia Fine Chemicals, Piscataway, N.J.; agarose; polystyrene beads about 1 micron to about 5 millimeters in diameter available from Abbott Laboratories of North Chicago, Ill.; polyvinyl chloride; polystyrene; cross-linked polyacrylamide; nitrocellulose; nylon-based webs such as sheets, strips or paddles; tubes, plates or the wells of a microtiter plate such as those made from polystyrene or polyvinylchloride; and the like.

Latex particles useful in agglutination-type assays are also useful solid matrices. Such materials are commercially available from Japan Synthetic Rubber Company of Tokyo, Japan, and are described as carboxy-functional particles dispersed in an anionic soap. Typical lots of such particles have an average diameter of 0.308 microns, and have an average carboxy-functional group distribution of about 15 to about 30 square Angstroms per carboxy group.

Prior to use, the particles are reacted with a diamine such as 1,3-diamino-2-propanol to form a plurality of amide bonds with the particle carboxy groups while maintaining free amine groups. The free amines are thereafter reacted with a dialdehyde such as glutaraldehyde and the antibody or antigen to form Schiff base reaction products. The Schiff base reaction products are thereafter reduced with a water-soluble reductant such as sodium borohydride to provide a useful solid support.

Those skilled in the art will understand that there are numerous methods of solid phase immunoassays that may be utilized herein. Exemplary, useful solid phase assays include enzyme multiplied immunoassay techniques (EMIT) and fluorescence immune assays (FIA), in addition to the specifically discussed ELISA. However, any method that results in a signal imparted by the reaction of anti-GCL-1 antibody with the lectin of this invention is suitable. Each of those assay methods can employ single or double antibody techniques in which an indicating means is utilized to signal the immunoreaction, and thereby the binding of an antibody that is to be assayed with the lectin of this invention. Exemplary techniques can be found explained in Maggio, *Enzyme Immunoassay,* CRC Press, Cleveland, Ohio (1981); and in Goldman, *Fluorescent Antibody Methods,* Academic Press, New York, N.Y. (1980).

One embodiment of a specific method for assaying a body fluid sample for anti-GCL-1 antibody is a noncompetitive ELISA wherein the immunoreactions are performed sequentially. In such an assay an aliquot of the lectin of this invention, e.g., generally about 1 to about 500 ug, is affixed to the inner walls of a microtiter well to form a solid support.

Any anti-GCL-1 antibody present in the body sample provided is then immunoreacted with the solid phase lectin. This is accomplished by admixing an aliquot, e.g., about 10 to about 200 ml of sample (which may be prediluted) such as serum of plasma in the microtiter well with the solid phase affixed lectin to form a solid/liquid phase admixture. The admixture is maintained for a predetermined time period sufficient for any anti-GCL-1 antibody present in the sample to immunologically bind to the lectin molecules and form a solid phase immunoreactant. The solid and liquid phases are thereafter separated, and the solid phase is typically rinsed to help assure removal of nonspecifically bound materials.

Anti-GCL-1 antibody present as solid phase immunoreactant (i.e., anti-GCL-1 bound to solid phase affixed lectin) is then immunoreacted with enzyme labeled second antibodies. This is accomplished by admixing an aliquot, e.g., about 0.1 to about 10 ug of enzyme labeled second antibodies in an aqueous buffer solution, preferably HRP—labeled goat anti-human Ig antibodies, to form a second solid/liquid admixture. The second admixture is maintained as described hereinabove, thus forming a solid phase immunoreactant "sandwich" consisting of lectin, anti-GCL-1 antibody and enzyme labeled antibodies.

After separating the liquid phase from the solid phase as previously described, an aliquot of chromogenic substrate, such as o-phylenediamine (OPD) in the presence of hydrogen peroxide for HRP, is admixed in the microtiter well containing solid phase immunoreactant to form a third solid/liquid admixture. This admixture is maintained for a predetermined time period sufficient for any enzyme present as immunoreactant to convert a proportional amount of substrate into product. The optical density of the resulting colored solution is then measured and compared to results obtained using solutions containing known amounts of reagent.

A diagnostic system, preferably in a kit form, useful for carrying out the anti-GCL-1 antibody methods of this invention includes, in combination but in separate packages, (a) the isolated lectin of this invention and (b) a labeled antibody for signaling the immunoreaction of anti-GCL-1 antibodies with the lectin. Preferably, the labeled antibody is whole antibody linked to an enzyme.

In preferred embodiments the system further includes a solid matrix to which the lectin can be affixed to form a solid support. Useful solid matrices have already been described. Preferably, however, the solid matrix is the well of a microtiter plate.

In further preferred embodiments the system also includes antibodies raised to the lectin of this invention as a positive control.

Known amounts of the lectin and labeled antibodies are provided. Those amounts are at least enough to carry out one assay. The lectin and labeled antibodies are typically provided in a form and amount that is designed to be diluted to a prescribed volume with water, saline or a buffer such as is known in the art.

Additional packages may also be included in the system. Such packages may contain (1) buffer salts in dry or liquid form, (ii) enzyme substrates such as o-phenylenediamine, and the like.

A method of asaying for the presence of GCL-1 in a body sample is also contemplated herein. In general, a body sample such as a cervical or urogenital smear to be assayed is provided, and is admixed with antibodies that contain an antibody combining site induced by the lectin of this invention. The admixture is maintained under biological assay conditions for a predetermined period of time sufficient for the antibody molecules to immunoreact with GCL-1 present in the body sample. The amount of that immunoreaction is then measured to determine whether GCL-1 molecules were present or absent in the assayed body sample.

One such exemplary embodiment is an immunofluorescent assay in which a cervical or urogenital smear is acetone-fixed to a plain microscope slide. An aliquot of antibodies raised in accordance with this invention, e.g., raised in rabbits, generally about 10 micrograms to about 5000 micrograms, is incubated on the slides using well-known techniques.

After rinsing away any un-immunoreacted antibodies and blocking non-specific binding sites on the slide with a protein such as BSA, a second antibody, such as a goat-anti rabbit antibody can then be incubated on the test slide, if desired. The second antibody is labeled by being linked to a fluorochrome dye such a fluorscein isothiocyanate (FITC).

After this second incubation, any excess of the second antibody is rinsed off leaving any FITC-labeled goat-anti rabbit antibodies that bound to the first antibodies on the test slide. Presence of the FITC-labeled antibodies may be detected using fluorescent microscopy and thereby signal the presence of a *N.gonorrhoeae* infection.

The indicating means is packaged separately from the antibodies when not linked directly to a antibodies of this invention. When admixed with a body sample such as an acetone-fixed cervical or urogenital smear, the antibodies immunoreact with the GCL-1 to form an immunoreactant, and the indicating means present then signals the formation of immunoreaction product.

The present invention is further illustrated by the following examples.

EXAMPLE 1

Production and Isolation of GCL-1

Piliated transparent and non-piliated transparent variants of the N.g. strain MS11 as well as the C9 strain of N.g. were grown on GCB plates (29 g GC Medium Base, Difco, 1 g Bacto-agar, Difco, 8 ml supplement A (400 g glucose, 10 g L-glutamine, 20 mg cocarboxylase/liter), and 0.8 ml supplement B (1.25 g Fe(-NO$_3$/250 ml) per 800 ml total volume). Piliation and transparent phenotypes were distinguished by the system described in James et al., Infect. Immun. 19:332-340 (1978), and Swanson, J., Infect. Immun. 19:320-331 (1978).

Plates were seeded and incubated for 18 hours in a 5% CO$_2$ atmosphere at 35° C. The obtained bacterial lawns were harvested by first admixing 1.25 ml of 50 mM tris buffer [tris(hydroxymethyl)aminomethane, Sigma Chemical Co., St. Louis, Mo. (pH 9.5)] to each plate. The cells in the harvested lawns were then loosened and transferred to 50 ml polycarbonate centrifuge tubes using a Pasteur pipet and stored at 0° C.

Subsequently, the stored cells were vortexed for 3 minutes to shear the bacterial surface proteins. The resulting suspension was then centrifuged or 20 minutes at 4° C. at 10,000 rpm in a Beckman JA-20 rotor to produce a pilin protein containing pellet and a GCL-1 containing supernatant. The supernatant was retained and dialyzed against Pili Buffer (150 mM tris, 150 mM NaCl, pH 7.5) for 24 hours at 4° C. using 6,000 to 8,000 molecular weight dialysis cutoff membrane (Spectropor, Fischer Scientific Co., Springfield, NJ) so as to effect protein aggregation and precipitation. The precipitated proteins were collected as a pellet after centrifugation as previously described. The pellet was resuspended in 10 ml of 50 mM tris (pH 9.5) thereby forming a crude GCL-1 extract. The crude extract was stored at −20° C.

An affinity absorbent for purifying GCL-1 was prepared by affixing gangliotetraosylceramide to a solid matrix. To each well of a polyvinyl chloride 96 well microliter plate was added 50 microliters of methanol containing 200 nanograms of gangliotetraosylceramide (Supelco Inc., Bellefonte, PA). The methanol was then allowed to evaporate leaving a deposit of gangliotetraosylceramide in each well. Non-specific binding sites in the wells were blocked by adding to each well 50 microliters of PBS containing 2% bovine serum albumin (BSA), maintaining the admixtures so formed for 4 hours at room temperature and then removing the excess blocking solution by inverting the wells and shaking.

GCL-1 was isolated by affinity adsorption from the above obtained crude extract by first introducing 50 microliters of crude extract into the microtiter wells having gangliotetraosylceramide affixed thereto. The resulting preparations were maintained for about 8 hours, thereby allowing GCL-1 present in the crude extract to bind to the gangliotetraosylceramide. Non-bound proteins were subsequently removed by inverting the wells and shaking. The wells were then rinsed five times with 50 microliter aliquots of PBS.

Specifically bound GCL-1 was eluted by adding 50 microliters of PBS containing 2% sodium dodecyl sulfate (SDS) to each well. The preparations made in this manner were maintained for 30 minutes at room temperature, thereby allowing resolution of the GCL-1 present. The obtained GCL-1 containing solution was then removed from the wells and stored at −20° C. Approximately one microgram of affinity isolated GCL-1 was thus obtained from each microtiter well.

In addition, GCL-1 was also isolated from the above obtained crude extract by Fast Protein Liquid Chromatography (FPLC) chromatofocusing. Crude GCL-1 extracts generated from the non-piliated N.g. strain MS11 variant B2 were first dialyzed against FPLC equilibration buffer (25 mM amidizole, pH 7.4) for 24 hours at 4 degrees C. using the aforementioned dialysis membrane so as to prepare the GCL-1 extract for chromatofocusing. Dialyzed GCL-1 extract was then applied to a Mono P chromatofocusing column (FPLC system, Pharmacia Inc., Piscataway, NJ) pre-equilibrated with FPLC equilibration buffer, and eluted with Polybuffer 74 (Sigma Chemical Co., St. Louis, MO) diluted 1:8 with sterile water and adjusted to pH 4.0.

The elution profile of a typical run of crude GCL-1 extract on such a chromatofocusing column is shown in FIG. 4. Eluant fractions were monitored for protein by measuring the optical density of the eluant at 280 nanometers (O.D. 280) and their pH was measured. Fractions containing protein eluted at a pH of about 6.1 to 6.4 were recovered and stored at −20 degrees C.

EXAMPLE 2

Molecular Weight Determination of Isolated Bacterial Lectin by SDS-PAGE

The relative molecular weight of the purified bacterial lectin produced in Example 1 was determined by SDS-PAGE according to the method of Laemmli, U.K., Nature 227:680-684 (1970). To that end, 12% and 15% polyacrylamide gels were cast and run with approximately 25 to 200 micrograms of total protein per lane. The following molecular weight marker proteins and their approximate molecular weights in daltons (d) were run in a control or standard lane: α-lactalbumin, 14,200; soybean trypsin inhibitor, 20,100; trypsinogen, 24,000; carbonic anhydrase, 29,000; glyceraldehyde-3-phosphate dehydrogenase, 36,000; egg albumin, 45,000; and bovine albumin, 66,000, all obtained from Sigma Chemical Corp., St. Louis, Mo.

After electrophoresis, protein bands were visualized by staining with coomassie brilliant blue (Sigma) or by the silver staining technique of Merril et al., Anal. Biochem. 105:361 (1980), using silver stain obtained from Bio-Rad, Richmond, CA.

Figure 1:
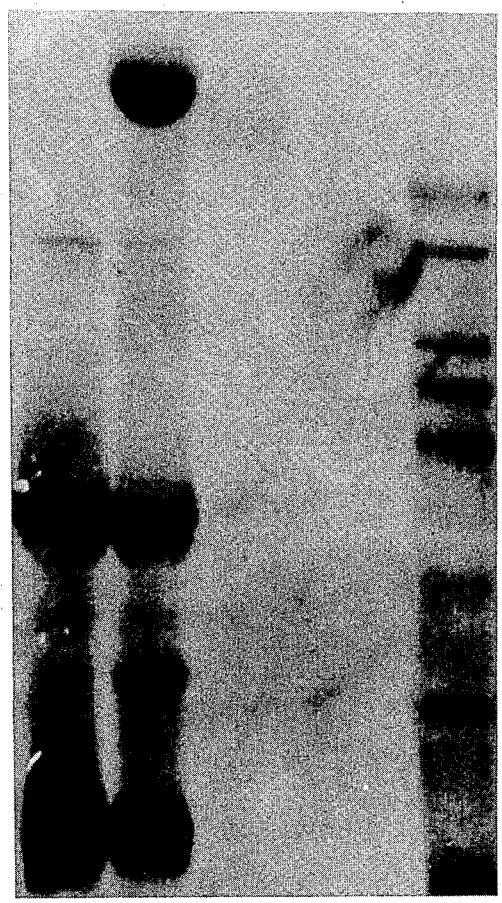
FIG. 1 is a photograph of a silver-stained 12% SDS-PAGE gel with the position of molecular weight marker proteins and their respective relative molecular weights in units of one thousand daltons shown to the right.

Analysis of the gels revealed one major band in the sample lane having a relative electrophoretic mobility greater than trypsinogen but less than soybean trypsin inhibitor and a relative molecular weight of about 22,400 daltons. This band, as shown in FIG. 1, is the affinity purified bacterial lectin GCL-1.

In some cases, the protein bands prior to staining were electrophoretically affixed to nitrocellulose (Schleicher & Schuell, Keene, NH, Catalog No. BA85)

to form Western blots as described in Towbin et al., Proc. Natl. Acad. Sci. USA 76:4350–4354 (1979). GCL-1 protein affixed to the nitrocellulose was detected by first immunoreacting the blots with rabbit anti-GCL-1 antibodies prepared by immunizing rabbits with the crude GCL-1 extract described in Example 1. The rabbit anti-GCL-1 antibodies immunologically bound to the nitrocellulose-affixed GCL-1 were then immunoreacted with alkaline phosphatase labeled goat anti-rabbit Ig. The presence of label, and thereby the presence of GCL-1, was visualized using the ProtoBlot immunoblotting system from Promega Biotech, Madison, WI (Catalog No. P3930).

Western blots of the products obtained from the various isolation steps of the affinity procedure described in Example 1 are shown in FIG. 2. Analysis of those blots reveals that affinity isolated GCL-1 is substantially free of other gonococcal pilin associated proteins.

A Western blot of a crude protein extract of *Morexella bovis* prepared in a manner similar to the N.g. crude extract described in Example 1 is shown in FIG. 3. Analysis of that blot reveals that *Morexella bovis* produces a protein that immunoreacts with anti-GCL-1 antibodies and has an apparent relative molecular weight of about 22,400 daltons.

EXAMPLE 3

Isolation and Characterization By 2D-PAGE

Crude, non-affinity purified bacterial surface protein extract containing GCL-1 produced in Example 1 was further isolated and characterized by 2D-PAGE using a System 2-D two dimensional gel system from Hoefer Scientific Instruments, San Francisco, CA. Isoelectric focusing (IEF) gels comprised of 6.5% polyacrylamide and two sets of ampholytes (LKB Instruments, Inc., Gaithersburg, MD), one set capable of producing a pH value gradient of 3 to 10 and another capable of producing a pH value gradient of 4 to 6.5 were prepared in 130×3 millimeter acid cleaned glass tubes. The gels were overlaid with either GCL-1 containing solution having approximately 25 micrograms of protein or a control solution containing the molecular weight marker proteins described in Example 2. A sample overlay solution [9 M urea, 2% of each of the above described ampholytes and 10% polyethylene(9)octyl phenyl ether (Nonidet P40)] was then overlaid on the gels. The proteins were subsequently subjected to electrophoresis at constant 400 volts for 12 hours and constant 800 volts for 1 hour.

The focused gels were removed from the tubes and washed twice for 30 minutes with treatment buffer (0.0625 M tris HCl, pH 6.8; 2% SDS; 10% glycerol; 5% 2-mercaptoethanol), thereby producing IEF gels containing proteins separated according to their isoelectric pH value.

The isoelectrically focused proteins were then separated according to their relative molecular weights by SDS-PAGE. The IEF gels were fixed to the top of 15% SDS-PAGE gels and run at about 30 milliamperes constant current using 0.1% phenol red as a tracking dye. When the tracking dye reached the bottom of the gel, electrophoresis was terminated. The gels were subsequently either stained with coomassie brilliant blue or silver stain as described in Example 2 or the proteins were transferred from the gels onto nitrocellulose as described in Towbin et al., supra.

Analysis of the gels revealed a single protein spot corresponding to a protein having a relative molecular weight of about 22,400 daltons, i.e., the relative molecular weight of GCL-1. The isoelectric pH value of this 22,400 dalton protein was about 6.1 to about 6.4.

EXAMPLE 4

Preparattion of Pure Gangliotetraosylceramide From Mouse Small Intestine

For the preparation of pure gangliotetraosylceramide from mouse small intestine, a series of extractions and chromatographic separations are conducted as follows. The solvents used are dried and redistilled before use.

Extraction

The small intestine is surgically removed from a mouse, cut into pieces and lyophilized to dryness. About 130 grams of lyophilized material is then subjected to extraction in two steps using a Soxhlet apparatus which is well known in the art. First, about 1000 milliliters of chloroform/methanol (2:1, by volume) is mixed with the lyophilized material in a 2000 milliliter round bottle and heated for about 24 hours at 70° C. in an asbestos insulated electrical heating device. After decanting the solvent, a second extraction of the material is similarly performed using 1500 milliliters of chloroform/methanol (1:9, by volume), and the solvent is decanted and added to the first. The combined solvent extracts are then evaporated to dryness under a stream of nitrogen.

Alkali Degradation

The dried intestinal extract is then alkali degraded by dissolving the extract in 500 milliliters of 0.2M KOH in methanol and the dissolved extract is maintained for 3 hours at room temperature in a glass bottle containing five glass beads which disperse the dried extract upon occasional shaking. Thereafter the obtained admixture is neutralized with 10 milliliters of glacial acetic acid, admixed with 1000 milliliters of chloroform/water (3:2, by volume), and dialyzed for 4 days against running tap water. The alkali degraded extract is then evaporated at 70° C. by first admixing thereto about 500 milliliters of toluene and then drying the obtained admixture using a roto-evaporator. The dried sample is then redissolved in about 500 milliliters of chloroform/methanol (2:1, by volume) and filtered to remove insoluble material. The filtration apparatus is washed to chase residual extract with about 500 milliliters of methanol. The filtrates are then combined, evaporated under a stream of nitrogen and redissolved in about 50 milliliters of chloroform.

Silicic Acid Chromatography

The alkali-degraded intestinal extract is then chromatographed on silicic acid columns to remove cholesterol and fatty acid methyl esters from glycolipids and alkali stable phospholipids.

Silicic acid (Malinckrodt Chem. Works, St. Louis, Mo.) of 100 mesh reagent grade is sieved into three particle sizes: less than about 44 micrometers (um), about 44–74 um, and more than about 74 um. The fraction less than about 44 um is washed by suspension in methanol (1 kilogram in 3 liters) followed by aspiration of the methanol layer after 30 minutes, to remove very small particles which could pass through the sintered glass filters at the bottom of the columns used in the procedures that follow.

Silicic acid particles fractionated to a size of about 44 to about 74 um are packed into a 50-gram column using chloroform, and the alkali degraded extract, previously redissolved in chloroform, is loaded onto the column. 500 Milliliters of chloroform followed by 500 milliliters of chloroform/methanol (98:2, by volume) are added to the column and allowed to flow through. Then 500 milliliters of chloroform/methanol (1:3, by volume) followed by 500 milliliters of methanol are added and the eluant from these two additions is collected, the eluants combined, and the liquid portions thereof evaporated under a stream of nitrogen to produce a dried extract.

Ion Exchange Chromatography

The dried extract from the silicic acid column is redissolved in about 10 milliliters of chloroform/methanol (2:1, by volume) and loaded onto a column of 20 grams of DEAE-cellulose (DE-23, Whatman Inc., Clifton, N.J.) packed in acetate form using chloroform/methanol (2:1, by volume). After about 1 to 2 days of equilibration time on the column at room temperature, the sample is eluted with 400 milliliters of chloroform/methanol (2:1, by volume) followed by 400 milliliters of methanol. The two eluants are combined and the liquid portion thereof evaporated under a stream of nitrogen to produce a dried extract.

Acetylation

Acetlation is performed by dissolving the DEAE column-eluted and dried extract in 10 milliliters of chloroform, admixing therewith 10 milliliters each of pyridine and acetic anhydride, and maintaining the admixture in the dark at room temperature for about 12 to 18 hours. After the acetylation reaction, 25 milliliters each of methanol and toluene are admixed and the sample is evaporated first under a stream of nitrogen while maintained at about 60° C. followed by evaporation to dryness using a roto-evaporator to produce an acetylated intestinal extract.

Silicic Acid Chromatography of the Acetylated Extract

The acetylated intestinal extract is redissolved in about 50 milliliters of chloroform and loaded onto a column containing 50 grams of silicic acid particles fractionated to a size of less than about 44 um and packed in chloroform/methanol (98:2, by volume). 500 Milliliters of chloroform/methanol (95:5, by volume) followed by 500 milliliters of chloroform/methanol (90:10, by volume) are added to the column and the eluants are collected, combined and the liquid portion thereof evaporated under a stream of nitrogen to produce a dried acetylated extract.

De-Acetylation

The silicic acid chromatographed and acetylated extract is then redissolved in about 20 milliliters of toluene/methanol/0.2 M KOH in methanol (1:1:2, respectively, by volume) and maintained with occasional shaking for 30 minutes at room temperature for de-acetylation to occur. After the reaction period, 2 milliliters of glacial acetic acid is admixed therewith, and the resulting admixture is transferred into 80 milliliters of chloroform/water (1:1, by volume) and dialyzed for 4 days against running tap water. The de-acetylated extract is then evaporated at 70° C. by first admixing about 100 milliliters of toluene and then drying the mixture using a roto-evaporator to produce a de-acetylated dried extract.

Chromatography Through a DEAE Cellulose Column

The de-acetylated dried extract is redissolved in about 10 milliliters of chloroform/methanol (2:1, by volume) and loaded onto a 10 gram column of DEAE-cellulose, and allowed to equilibrate as described hereinbefore. 250 Milliliters of chloroform/methanol (2:1, by volume) is then added to the column followed by 250 millliliters of methanol. The resulting eluants are combined and the liquid portions thereof evaporated under a stream of nitrogen to produce a glycolipid containing residue.

Silicic Acid Chromatography

An aliquot of the above-obtained residue is redissolved in 500 milliliters of chloroform/methanol (98:2, by volume) and loaded onto a 25 gram column of silicic acid of particle size less than about 44 um which is packed in the same solvent. 500 Milliliters of chloroform/methanol (98:2, by volume) is added to the column and allowed to flow through. Then 250 milliliters of chloroform/methanol (1:3, by volume) followed by 250 milliliters of methanol are added to the column and the eluants from these two additions are collected, combined and the liquid portion thereof evaporated under a stream of nitrogen. The resulting dried material is substantially pure gangliotetrasylceramide [Hansson et al., FEBS Letters, 139:291 (1982)].

EXAMPLE 5

Production of Isolated GCL-1 by Cloning of the Gene Encoding GCL-1 and Expression in Recombinant DNA Vectors The gene coding for GCL-1 contained in gonococcal DNA from the non-piliated variant B2 of the MS11 strain of N.g. was cloned and manipulated into expression vectors using procedures that are well known in the art and described in more detail in Maniatis et al., *Molecular Cloning: A Laboratory Manual*, Cold Spring Harbor Laboratories (1982).

To that end, DNA from the above N.g. variant was isolated, restriction digested with the enzyme MboI to a partial extent and inserted into the BamHI restriction site of the cloning vector pHSS6 described by Seifert et al., Proc. Natl. Acad. Sci. USA 83:735 (1986). The resulting recombinant plasmids were propagated in *E. coli* strain HB101 (Bethesda Research Laboratories, Gaithersberg, MD) as the biological host. The bulk of the different plasmid-containing *E. coli* were then screened as a library for those bacteria which contained a plasmid with the GCL-1 gene inserted therein.

The screening assay to identify bacteria that contain a plasmid with the GCL-1 gene inserted therein was accomplished by taking advantage of the ability of the GCL-1 gene product to be expressed within the *E. coli* by utilizing the GCL-1 gene's own, naturally-occurring promoter for expression. Expressed GCL-1 was detected in those bacterial colonies containing plasmids with the GCL-1 gene by immunoscreening the library of bacterial colonies using antisera raised in rabbits to GCL-1 isolated by chromatofocusing as described in EXAMPLE 1.

For the production of this antisera, about 10 to 20 micrograms of isolated GCL-1 was innoculated subcutaneously into the neck of a rabbit. The first innoculation was in complete Freund's adjuvant, followed twice at two week intervals with similar innoculation in incomplete Freund's adjuvant. Positive reacting antisera was identified by its ability to recognize GCL-1 in crude extracts on Western blots as described in EXAMPLE 2.

The immunoscreening procedure for identifying those *E. coli* bacteria in the library which express GCL-1 was carried out according to the procedure of Helfman et al., Focus 6:1-5 (1984), which is incorporated herein by reference, with the few exceptions listed below. Those exceptions were: substitution of non-fat dry milk in place of bovine serum albumin (BSA) as a blocking agent as described by Johnson et al., Gene Anal. Techn. 1:3-8 (1984), also incorporated herein by reference, and substitution of alkaline phosphatase labeled goat anti-rabbit immunoglobin in place of $^{125}$I-labeled second antibody as the indicating means. The presence of label, and thereby the presence of GCL-1, was visualized using the Protoblot Immunoblotting System from Promega Biotech, Madison, WI (Catalog No. P3930).

Individual positive reacting bacterial colonies containing GCL-1 as determined by the aforementioned immunoscreening procedure were recovered independently, and were colony purified at least once to assure homogeneity. Each isolate was then further analyzed for expression of GCL-1 by Western blotting as described in EXAMPLE 1. To that end, mini-cultures of individual bacterial isolates were lysed directly in SDS-PAGE sample buffer and resolved on Western blots which were developed using the aforementioned antisera raised against GCL-1 isolated by chromatofocusing. Representative bacterial cultures so analyzed and that express the GCL-1 are shown in FIG. 5.

The apparent mobility of GCL-1 expressed in *E. coli* corresponds to a relative molecular weight that is slightly larger than the lectin isolated directly from extracts of N.g. cultures. It is believed that the expression medium within the *E. coli* host does not process and cleave a leader sequence from the expressed protein, thereby resulting in a relatively larger protein product as that found in the host of the origin, i.e., N.g.

These representative cultures were further analyzed to determine the approximate size of the GCL-1-expressing DNA insert contained within the resident plasmid vector by well known techniques, including restriction enzyme digestion with the enzyme Not I. Inserts in a size of about 2.8 to about 4.0 kilobases (kb) were detected.

From the observed data the presence of numerous structural sequence characteristics of the produced non-chromosomal plasmid vectors can be inferred inasmuch as the general nature of such structural sequences is well known in the art. See, for example, Lewin, *Genes*, John Wiley & Sons, Ltd., New York, N.Y. (1983). More specifically, prokaryotic bacterial proteins are colinear with their cognate nucleotide sequence without any of the interruptions found in eukaryotes such as intervening, non-coding sequences (i.e., introns). Therefore, a rough estimation of the number of nucleotide base pairs that code for GCL-1 can be made directly from the apparent molecular weight of the lectin resolved with SDS-PAGE by using the conversion factors of about 110 daltons per amino acid residue and three nucleotide base pairs per amino acid residue. By this conversion GCL-1, having a size of about 22,400 daltons, contains about 204 amino acids and is coded for by about 612 nucleotide base pairs.

The expression of genes in bacteria is dependent upon start and stop signals for both transcription and translation. These signals are also called expression regulatory signals because they are signals contained within the sequence that regulate expression of the protein coding sequence. Because these signals are not present around the BamHI cloning site of the plasmid vector pHSS6, these sequences are provided by the DNA insert in their usual locations at or near the ends of that portion which codes for GCL-1. Thus, the inserted DNA fragment includes a coding region as well as the expression regulatory signals operatively linked upstream and downstream (flanking) as appropriate to the coding region for expression of the bacterial lectin, that are foreign to the biological host for the DNA insert.

The presence of a leader peptide, which is usual for proteins associated with membranes or for proteins to be secreted, is evidenced by the slightly larger apparent molecular weight of GCL-1 when expressed in *E. coli* instead of its natural biological host.

In addition, a specific component of the expression regulatory signals is the promoter that is required to initiate transcription of the GCL-1 gene. This promoter sequence is normally located 5' relative to the beginning of the coding sequence. Because the promoter sequence has been characterized in other bacterial genes, the GCL-1 promoter is also believed to be relatively closely linked to and located within about 100 nucleotide base pairs from the leader sequence at the 5' end of the coding sequence.

Accordingly, while the representative GCL-1 gene inserts characterized hereinabove have a size range of about 2.8 to about 4.0 kb, and comprise a coding sequence that codes for a lectin protein of about 22,400 daltons, such inserts can be much larger, i.e., of the order of about 10 kb, preferably about 6 kb. A leader sequence, appropriate start and stop signals including a promoter, and varying amounts of additional superfluous flanking sequences located at either or both ends of the gene may be present in addition to the GCL-1 gene itself in the cloned and isolated DNA fragments contemplated by the present invention.

A representative *E. coli* isolate containing the pHSS6 plasmid as expression vector with a GCL-1 gene inserted therein, and which expressed GCL-1 as shown in FIG. 5, was given the designation pGCL-1 for reference purposes. This bacterial culture has been deposited with the American Type Culture Collection (ATCC), Rockville, Md. under the ATCC Accession Number 67,198.

The deposit was made in compliance with the Budapest Treaty requirements that the duration of the deposit should be for 30 years from the date of deposit or for 5 years after the last request for the deposit at the depository or for the enforceable life of a U.S. patent that matures from this application, whichever is longer. The recombinant plasmid-containing cells will be replenished should they become non-viable at the depository.

Accordingly, the present invention, in one aspect, contemplates a DNA fragment either isolated or as a replicable DNA fragment in a biological host, but foreign to that host, which fragment encodes for a bacterial lectin as characterized hereinabove. This DNA fragment can include the regulatory signals for expression of the contemplated bacterial lectin operatively linked to the coding region for that lectin present in the DNA fragment. While these expression regulatory signals are foreign to the biological host, the signals are recognized by the host. In a preferred embodiment of this particular aspect of the present invention, the coding region is the naturally-occurring coding region for the lectin present in N.g. for that lectin. More preferably, the expression regulatory signals or signal base pair sequences that are present in the DNA fragment are the naturally-occurring N.g. expression regulatory signals associated with the N.g. coding region for the lectin.

The coding region for the bacterial lectin contemplated herein contains no more than about 650 base pairs and is associated with flanking regions that are linked thereto at both ends. The flanking regions together with the coding region contain no more than about 10 kb pairs, preferably no more than about 6 kb pairs.

A further method aspect of the present invention contemplates a method of producing a bacterial lectin utilizing the steps of growing, under appropriate conditions, a bacterial culture that comprises bacteria that contain a non-chromosomal plasmid vector as described hereinabove for propagating DNA in a transcription-translation medium and thereafter harvesting the expressed bacterial lectin from the culture utilizing well known protein harvesting techniques.

The foregoing specification, including the specific embodiments, is intended to be illustrative of the present invention and is not to be taken as limiting. Numerous other variations and modifications can be effected without departing from the true spirit and scope of the present invention.

We claim:

1. An isolated bacterial lectin, obtainable from gonococci, having a relative molecular weight of about 22,400 daltons, as determined by sodium dodecyl sulfate-polyacrylamide gel electrophoresis, and an isolectric pH value in the range of about 6.1 to about 6.4; said lectin having the ability to bind specifically gangliotetraosylceramide.

2. The bacterial lectin of claim 1 in the form of a pharmaceutically acceptable salt.

3. An inoculum which comprises the isolated bacterial lectin of claim 1 together with a pharmaceutically acceptable carrier therefor.

4. The inoculum in accordance with claim 3 and in unit dose form wherein the lectin is present in an amount of about 10 micrograms to about 500 milligrams.

5. The inoculum in accordance with claim 3 and in unit dose form wherein the lectin is present in an amount of about 100 micrograms to about 500 milligrams.

6. A method of immunizing a human against a gonococcal infection which comprises administering to the human an effective amount of the lectin defined in claim 1 in a pharmaceutically acceptable carrier.

7. The method in accordance with claim 6 wherein about 100 micrograms to about 100 milligrams of the lectin are administered to the human.

8. A method for determining the presence of lectin GCL-1 in a human's body sample comprising the steps of (a) obtaining a body sample from the human;
(b) combining the obtained body sample with antibodies to GCL-1 so as to form an immunoreaction admixture;
(c) maintaining the formed immunoreaction mixture at biological assay conditions for a time period sufficient for the anti-GCL-1 antibodies to bind to any GCL-1 present in said body sample, thereby forming an immunoreactant; and
(d) assaying the maintained admixture for the presence of the immunoreactant.

9. A method for determining the presence of anti-GCL-1 antibodies in a human's body sample comprising the steps of (a) obtaining a body sample from the human;
(b) combining the obtained body sample with an aliquot of the isolated bacterial lectin defined in claim 1 so as to form an immunoreaction admixture;
(c) maintaining the formed admixture at biological assay conditions for a time period sufficient for the isolated bacterial lectin to bind to anti-GCL-1 antibodies present in said body sample, thereby forming an immunoreactant; and
(d) assaying the maintained admixture for the presence of the immunoreactant.

10. A diagnostic system suitable for assaying for *Neisseria gonorrhoeae* lectin GCL-1, which system comprises, in combination: (a) antibodies to the lectin GCL-1 as defined in claim 1 and (b) indicator means capable of signaling an immunoreaction of said antibodies with said lectin GCL-1.

11. A diagnostic assay system suitable for determining the presence of anti-GCL-1 antibodies in a body sample which system comprises, in combination: (a) the isolated bacterial lectin defined by claim 1 and (b) indicating means capable of signaling an immunoreaction of said antibodies with the lectin.

12. A method of inducing in a warm-blooded animal production of antibodies that immunoreact with lectin GCL-1 as defined by claim 1 which comprises administering to said animal an inoculum containing an effective amount of said lectin in a pharmaceutically acceptable carrier therefor.

13. The method in accordance with claim 12 wherein the inoculum also contains an adjuvant.

14. An isolated DNA fragment capable of expressing the bacterial lectin of claim 1 when contained in an expression vector; said DNA fragment having a coding region for said lectin of no more than about 650 base pairs and a flanking region linked on either side thereof, and said flanking regions together with said coding region containing no more than 10 kb pairs.

15. The isolated DNA fragment in accordance with claim 14 and having no more than about 6 kb pairs.

16. A biological host having a replicable DNA fragment that has a coding region encoding the bacterial lectin of claim 1; said DNA fragment being foreign to said biological host.

17. The biological host in accordance with claim 16 wherein said DNA fragment further includes regulatory signals for expression of said lectin that flank said coding region; said expression regulatory signals being recognized by said biological host but being foreign to said biological host.

18. The biological host in accordance with claim 16 wherein said coding region is the naturally-occurring coding region of *Neisseria gonorrhoeae* for said lectin.

19. The biological host in accordance with claim 18 wherein said DNA fragment further includes, flanking said naturally-occurring coding region, the naturally occurring *Neisseria gonorrhoeae* expression regulatory signals for expression of said lectin.

20. A non-chromosomal plasmid vector for propagating DNA in a transcription-translation medium comprising a DNA fragment capable of expressing the bacterial lectin of claim 1 and operatively linked to base pair sequences regulating replication and expression of said DNA fragment, said fragment having a coding region for said lectin of no more than about 650 base pairs and flanking regions linked thereto and together with said coding region containing no more than about 10 kb pairs.

21. A bacterial culture comprising bacteria that contain the plasmid vector of claim 20 and a medium appropriate for the expression of the lectin coded for by the DNA fragment contained therein.

22. The bacterial culture of claim 21 in which said bacterial culture is identified by ATCC Accession Number 67,198.

23. A method of producing a bacterial lectin comprising the steps of:
(1) growing a bacterial culture comprising bacteria that contain a non-chromosomal plasmid vector for propagating DNA in a transcription-translation medium which vector contains a DNA fragment capable of expressing the bacterial lectin operatively linked to base pair sequences regulating replication and expression of said DNA fragment under growth conditions appropriate for the bacterial lectin to be expressed in said culture, and
(2) harvesting the expressed bacterial lectin from the bacterial culture.

* * * * *

UNITED STATES PATENT AND TRADEMARK OFFICE
CERTIFICATE OF CORRECTION

PATENT NO. : 4,786,592

DATED : November 22, 1988

INVENTOR(S) : Carolyn D. Deal et al.

It is certified that error appears in the above-identified patent and that said Letters Patent is hereby corrected as shown below:

Column 1, after the title and before the heading "CROSS-REFERENCE TO RELATION APPLICATION", insert the following paragraph:

--This invention was made with government support under Contract Nos. AI 20845 and AI 22152 awarded by the National Institutes of Health. The government has certain rights in the invention.--

Signed and Sealed this

First Day of February, 1994

*Attest:*

BRUCE LEHMAN

*Attesting Officer*     *Commissioner of Patents and Trademarks*